United States Patent
Kasprzak et al.

(10) Patent No.: US 7,255,828 B2
(45) Date of Patent: Aug. 14, 2007

(54) ELECTROMAGNETIC METHOD AND APPARATUS FOR TREATMENT OF ENGINEERING MATERIALS, PRODUCTS, AND RELATED PROCESSES

(76) Inventors: Marcin Stanislaw Kasprzak, Wschodnia 1 No. 24, 41-707 Ruda Slaska 7 (PL); Wojciech Kasprzak, 154 Campbell Avenue, Windsor, Ontario (CA) N9B 2H2; Jerzy H. Sokolowski, 3683 Inglewood Avenue, Windsor, Ontario (CA) N9E 43

(*) Notice: Subject to any disclaimer, the term of this patent is extended or adjusted under 35 U.S.C. 154(b) by 552 days.

(21) Appl. No.: 10/727,605

(22) Filed: Dec. 5, 2003

(65) Prior Publication Data

US 2004/0108630 A1 Jun. 10, 2004

Related U.S. Application Data (60) Provisional application No. 60/431,236, filed on Dec. 6, 2002.

(51) Int. Cl.
C21D 11/00 (2006.01)
C21B 7/24 (2006.01)

(52) U.S. Cl. .......................... 266/87; 266/80
(58) Field of Classification Search .................. 266/80, 266/87
See application file for complete search history.

(56) References Cited

U.S. PATENT DOCUMENTS

| 2,963,758 | A |  | 12/1960 | Pestel et al. |
| 3,153,820 | A |  | 10/1964 | Criner |
| 4,523,628 | A |  | 6/1985 | Vives |
| RE32,529 | E |  | 10/1987 | Vives |
| 4,897,518 | A | * | 1/1990 | Mucha et al. ................ 266/80 |
| 4,927,460 | A | * | 5/1990 | Simcock ..................... 266/234 |
| 2005/0151306 | A1 | * | 7/2005 | Sokolowski et al. .......... 266/80 |

FOREIGN PATENT DOCUMENTS

WO PCT/CA02/01903 12/2002

OTHER PUBLICATIONS

U.S. Appl. No. 60/339,358, filed Dec. 2001, Kasprzak et al.
Vives, Charles, Effects of Forced Electromagnetic, no date.

* cited by examiner

Primary Examiner—Scott Kastler
(74) Attorney, Agent, or Firm—Dennis R. Haszko (57) ABSTRACT

A method and apparatus for performing electromagnetic treatment on engineering materials and products and for improving processing technologies and service characteristics of the materials. The apparatus integrates electromagnetic treatment with a thermal analyzer and a control system. The apparatus allows for precise control of the operating parameters of an electromagnetic treatment process in order to render significant improvement in the materials and products metallurgical characteristics.

3 Claims, 8 Drawing Sheets

ELECTROMAGNETIC METHOD AND APPARATUS FOR TREATMENT OF ENGINEERING MATERIALS, PRODUCTS, AND RELATED PROCESSES

RELATED APPLICATIONS

The present invention claims priority from U.S. Provisional Patent Application Ser. No. 60/431,236 filed on 6 Dec. 2002.

BACKGROUND OF THE INVENTION

Field of the Invention

The present invention relates to an apparatus and a method that uses electromagnetic forces to improve engineering materials, processes, and products. More specifically, the present invention provides an apparatus and method that uses precisely controlled electromagnetic forces to stir and vibrate a work piece in order to improve the work piece's metallurgical micro and macro structures as well as its service characteristics.

DESCRIPTION OF THE PRIOR ART

It is known that metals and alloys such as steel and aluminum, can be cast, in the form of billets, plates or ingots, or shaped components, either by casting in a mould or by vertical or horizontal continuous casting. In some conventional processes, a mould is filled with a known amount of liquid metal, and the liquid metal is solidified within the mould, by heat exchange with the wall of the mould.

In other conventional processes, the metal, in a molten condition, is poured into a mould which generally has a vertical axis of symmetry and which is open at its two ends and the side walls of which are cooled by a fluid. On coming into contact with the mould, the metal sets to form a crust which gradually increases in thickness as the ingot advances through the mould, whereby, at the lower end of the mould, the thickness of the crust is sufficient to retain the central part which is still in a liquid state. After it has left the mould, the wall of the ingot is cooled directly by spraying water thereupon, thereby fairly quickly causing complete solidification of the metal mass.

In both such conventional processes, the ingot produced is in a highly heterogeneous condition. Such ingot has both a cortical region that is formed by rapid solidification, in contact with the mould, and a central region that results from a slower rate of cooling by heat exchange with the wall of the mould or with the water, through the cortical region. As those regions crystallized at different rates, they do not have the same structure or the same composition. In addition, the skin or surface layer that is formed on the ingot in contact with the mould is generally irregular. Therefore, in most cases the ingots have to be subjected to supplementary scalping or decrusting operations in order to remove the faulty regions to prevent the occurrence of defects resulting in the course of the subsequent stages of transforming the ingot.

Accordingly, in order to enhance the quality of products produced by a casting process, the man skilled in the art has sought solutions to such problems of heterogeneity of surface and structure. In the field of treatment of engineering materials, it is known that electromagnetic forces impacted on materials improve their structural characteristics. For example, in U.S. reissue patent RE 32,529 and U.S. Pat. No. 4,523,628, there are disclosed processes for improving the structure and the surface conditions of cast products by using stationary and variable electromagnetic fields simultaneously in order to produce radial vibrations in a non solidified metal. However, neither of the above technologies provide for a wide range of precisely controlled electromagnetic forces to be imposed on processed materials and products to refine the metal grain size and structure, thereby significantly improving the metallurgical characteristics of final products.

U.S. Pat. No. 2,963,758 claims a process for reducing the development of basaltic grains, which comprises subjecting the metal, in a molten condition, to a magnetic field, in the direction of the thermal gradient of cooling of the ingot, and continuously displacing said field in a direction substantially perpendicular to the direction of said gradient. The generation of the magnetic field requires the use of a six-pole stator connected to a source of polyphase electrical current. That means that the installation is fairly complicated and the efficiency thereof is subjected to limits imposed by the size of the grains.

In U.S. Pat. No. 3,153,820, the invention concerns an apparatus for improving the physical and chemical homogeneity and structure of the cast metal, by controlling the solidification process. That apparatus comprises, in combination, a plurality of independently operating, external agitators, including electromagnets and electromechanical vibration transducers disposed outside the mass of metal, being regularly spaced and disposed close to the region of cooling of the metal, said agitators producing a plurality of agitation force fields which are concentrated within the metal. Although such an apparatus, which includes several types of devices of fairly complicated design, reduces the phenomena of segregation within the metal, it does not solve the problems concerning the surface condition.

None of the prior art provides both suitably homogenous structures and surface conditions substantially free of defects. Furthermore, none of the above technologies provide the ability to perform advanced thermal analysis on a work piece during electromagnetic treatment.

What is needed therefore is an apparatus that improves the final product characteristics of engineering materials, processes and products while substantially reducing their production time and costs. More specifically, such an apparatus is needed that can generate and control electromagnetic stirring and vibration conditions to engineering materials to process under closed-loop controlled conditions using a wide range of operating parameters leading to improved product characteristics.

SUMMARY OF THE INVENTION

The present invention provides an apparatus that performs electromagnetic treatment of metallurgical materials and products. The present invention also provides the ability to analyze the properties of a work piece at various stages of an electromagnetic treatment in order to determine the effects of the treatment on the properties of the work piece with a high degree of accuracy and precision.

According to a first aspect, the present invention provides an apparatus for performing electromagnetic treatment on processed metallurgical materials and products, said apparatus comprising: a holder for a work piece; a power supply for providing voltage and current to at least one electromagnetic coil; a thermal source for varying temperature of said work piece and each electromagnetic coil; at least one sensor; a data acquisition means for recording data measured by at least one sensor, and a processor for controlling, monitoring, and analyzing at least one operating parameter of said electromagnetic treatment; wherein said power supply is coupled to each electromagnetic coil, said holder is located proximate to said electromagnetic coil, said thermal source is coupled to said holder and said electromagnetic coil, and said processor is coupled to said power supply, said data acquisition means, and said thermal source.

According to a second aspect, the present invention provides an apparatus for performing electromagnetic treatment and thermal-chemical treatments simultaneously on processed engineering materials and products, said apparatus comprising: a holder for a work piece; a power supply for providing voltage and current to at least one electromagnetic coil; a heating/cooling source for varying the temperature of said work piece and each electromagnetic coil; a thermo-chemical treatment system; at least one sensor; a data acquisition means for recording data measured by at least one sensor; and a processor for controlling, monitoring, and analyzing at least one operating parameter of said electromagnetic treatment; wherein said power supply is coupled to each electromagnetic coil, said holder is located proximate to said electromagnetic coil, said heating/cooling source is coupled to said holder and said electromagnetic coil, said thermo-chemical treatment system is connected to said work piece, and said processor is coupled to said power supply, said data acquisition means, and said thermal source.

According to a third aspect, the present invention provides an apparatus for optimizing electromagnetic treatment processes for processed engineering materials and products, said apparatus comprising: a holder for a work piece; a power supply for providing voltage and current to at least one electromagnetic coil; a thermal source for varying the temperature of said work piece and each electromagnetic coil; at least one sensor, a data acquisition means for recording data measured by at least one sensor; and a computer for controlling, monitoring, and analyzing at least one operating parameter of said electromagnetic treatment and for adjusting at least one operating parameter based on said data acquired by said data acquisition means; wherein said power supply is coupled to each electromagnetic coil, said holder is located proximate to said electromagnetic coil, said thermal source is coupled to said holder and said electromagnetic coil, said computer is coupled to said power supply, said data acquisition means, and said thermal source, said computer uses an Advanced Thermal Analysis (ATA) technique to analyze the thermal signature of said work piece during said electromagnetic treatment.

According to a fourth aspect, the present invention provides a method for optimizing electromagnetic treatment processes for processed metallurgical materials and products, said method comprising the steps of: applying, at a given temperature, an Electromagnetic (EM) Field to a work piece; measuring operating parameters of said electromagnetic treatment process; recording and storing said measured operating parameters in a database; and applying heating, cooling, or isothermal holding cycles to said work piece; adding chemical additives to improve certain metallurgical characteristics of said work piece; analyzing physical characteristics of said work piece during and after the completion of said electromagnetic treatment process; wherein said method is repeated until said physical characteristics of said work piece are optimized.

According to a fifth aspect, the present invention provides a method for optimizing electromagnetic treatment processes for processed metallurgical materials and products, said method comprising the steps of: applying, through a temperature range, an Electromagnetic (EM) Field to a work piece; measuring operating parameters of said electromagnetic treatment process; recording and storing said measured operating parameters in a database; and applying heating, cooling, isothermal holding cycles to said work piece; adding chemical additives to improve certain metallurgical characteristics of said work piece; analyzing physical characteristics of said work piece during and after the completion of said electromagnetic treatment process; wherein said method is repeated until said physical characteristics of said work piece are optimized.

According to a sixth aspect, the present invention provides a method for optimizing electromagnetic treatment processes for processed metallurgical materials and products, said method comprising the steps of applying, for a given time period, an Electromagnetic (EM) Field to a work piece; measuring operating parameters of said electromagnetic treatment process; recording and storing said measured operating parameters in a database; and applying heating, cooling, isothermal holding cycles to said work piece; adding chemical additives to improve certain metallurgical characteristics of said work piece; analyzing physical characteristics of said work piece during and after the completion of said electromagnetic treatment process; wherein said method is repeated until said physical characteristics of said work piece are optimized.

DETAILED DESCRIPTION OF THE INVENTION

The invention will be described for the purposes of illustration only in connection with certain embodiments; however, it is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

The Integrated Electromagnetic Stirring and Vibration (IESV) method and apparatus allows for a wide range of precisely controlled electromagnetic forces to be imposed on processed materials and products. In turn, the utilization of the apparatus results in considerably refined micro and macro metallurgical structures as well as service characteristics of treated materials and products. For some applications, electromagnetic treatment can be carried out simultaneously with thermo-chemical treatments.

All of these treatments can be performed above liquidus temperature, prior to and after the dendrite coherency point temperature as well as during the whole solidification process. Electromagnetic treatment can also be carried out during the heat treatment of semi-solid and/or solid materials.

The present invention can be used for both, low volume and mass production of simple and complex shaped products. In addition, this apparatus can be utilized for rapid and scientifically controlled development and improvement of engineering metals, alloys and metal matrix composites and their metallurgical and physical-chemical processes for the manufacturing of cast and plastically formed products (including shaped and continuous ones). The computerized closed-loop apparatus is based on the Integrated Electromagnetic Stirring and Vibration (IESV) phenomenon combined with Thermal Analysis (TA). Such treatments can be performed under a controlled processing environment.

The IESV system can either operate as a stand-alone workstation or can also be integrated with various industrial equipment and processing technologies as well as laboratory analytical and testing instruments.

The aforementioned method and apparatus for IESV applications improves the final product characteristics and its processing technology, along with substantially reducing production time and costs, in turn maximizing productivity.

In one embodiment, the present invention comprises a multifunctional electromagnetic coil(s) (MEC), a least one electromagnetic core, a power supply, termed a controlled current/voltage source, a multifunctional heating/cooling system, a multifunctional protective system (MPS) of the work piece(s) environment, thermo-chemical treatment system of the work piece(s), IESV treatment crucible(s)/Cell(s), IESV Sensor(s), and IESV software.

The Multifunctional Electromagnetic Coil(s) (MEC) is connected to the Controlled Current/Voltage Power Source(s) (CCVPS(s)) and is the source of finely tuned electromagnetic forces generated within the work piece(s). The MEC(s) is capable of treating liquid, semi-solid and/or solid state engineering materials and/or products (metals, alloys or metal matrix composites, castings, wrought products, etc.) during IESV operations.

The quantity, shape and dimensions of the Multifunctional Excitation Coil(s) and its conductors are capable of accommodating diverse shapes, dimensions and quantity of the processed product(s) as well as manufacturing/testing operation(s), including continuous and batch processes.

The Electromagnetic Core(s) (EC) are located in the close vicinity of the Multifunctional Electromagnetic Coil(s), allowing for considerably increased electromagnetic field intensity and its spatial distribution.

The Power Supply termed Controlled Current/Voltage Source(s) (CCS) is connected to the Multifunctional Electromagnetic Coil(s) and has the capabilities of: a) Generating an Alternative Current (AC) component having harmonic shapes (i.e. sinusoidal, rectangular, triangular, etc. with controlled characteristics; b) Imposing a Direct Current (DC) with a constant bias on the AC Current; and c) Varying the frequency $f$ of the AC current component.

It should be noted that computer software controls the operating parameters of the CCS power supply and allows for a desired setup of the AC and DC operating parameters.

The computer controlled Multifunctional Cooling/Heating System is capable of: a) Protecting the Multifunctional Electromagnetic Coil(s) against both, the heat generated in the processed work piece(s) and in the coil(s) itself, b) Controlled cooling of the work piece (s) by delivering the cooling medium(s) to internal and/or external surfaces; c) Controlled heating, isothermal holding etc. of the work piece(s) during the System's operation; and d) Controlled heating and cooling cycles are superimposed on the work piece(s) in a desired sequence/pattern. The work piece(s) spatial temperature gradients and the dynamic control of individual metallurgical reactions are carried out during electromagnetic treatment.

The Multifunctional Protective System of the Work Piece(s) Environment is capable of providing the environment with protective gases against degradation of the work piece(s) during the System's operations.

The Thermo-Chemical Treatment System of the Work Piece(s) liquid, semi-solid, and solid) performs simultaneous and independent operations using additives such as neutral and reactive gases, solids and powders. In addition, the chemical treatment can be performed either with or without the imposed programmable thermal cycle during electromagnetic treatment.

The Treatment Crucible(s)/Cell(s) containing the liquid/semi-liquid/solid work piece(s) is placed in the electromagnetic field generated by the Multifunctional Electromagnetic Coil(s). For all electromagnetic treatment applications, the Crucible(s)/Cell(s) must be made of non-magnetic material(s). For safety reasons and thermal protection of the Multifunctional Electromagnetic Coil(s), insulation of the work piece(s) is required in some applications.

The IESV Sensor(s) is capable of measuring the system's operating parameters such as; electromagnetic field intensity, temperature, flow rate, etc. A High Speed Data Acquisition System records each of the sensor(s) signals. Software based on the sensor(s) feedback signals controls the System's operations.

The IESV Software is capable of on and off-site programming, monitoring and controlling: a) operational conditions of the Controlled Current/Voltage Source(s) during the electromagnetic treatment process(es) of the work piece(s); b) variable heating and cooling operational parameters; and c) variable parameters of the Thermo-Chemical Treatment System and the Multifunctional Protective System of the Work Piece(s) Environment.

Moreover, the IESV Software is capable of collecting, storing and analyzing the sensor(s) signal(s) in the System's database and producing a hard copy report. The thermal signature of the treated work piece(s) is analyzed by the Advanced Thermal Analysis (ATA) technique for optimization of work piece(s) characteristics and process parameters as well as dynamic process control.

According to the preferred embodiment, the IESV apparatus allows for precisely controlled electromagnetic forces to be imposed on processed materials and products, resulting in refined micro and macro metallurgical structures and service characteristics of treated materials and products. Furthermore, the IESV apparatus allows for electromagnetic treatment to be performed simultaneous with thermo-chemical treatments.

The IESV apparatus includes, a multifunctional electromagnetic coil, a means for housing a work piece, a heating/cooling means, a power supply and a programmable data acquisition and control means. In accordance with present the invention, the multifunctional electromagnetic core is located in close vicinity of the electromagnetic core, thereby allowing for increased electromagnetic field intensity and spatial distribution. It should be understood that any suitably shaped electromagnetic coil could be provided without straying from the intended scope of the invention. In the preferred embodiment, the power supply is a controlled current/voltage source, which generates an alternating current (AC) component having harmonic shapes and a direct current (DC) component with a constant bias.

In an embodiment of the invention, the means for housing a work piece is a crucible, which is placed inside the electromagnetic core. It should be noted that for proper operation of the apparatus of the present invention, the crucible must be made from non-magnetic material. Furthermore, it should be noted that for safety reasons and thermal protection of the MEC, insulation of the work piece may be required.

The IESV apparatus also contains sensors that are capable of measuring operating system parameters such as electromagnetic field intensity, temperature and flow rate. It should be readily understood that any type of sensor known to one skilled in the art are used for sensing purposes discussed herein without straying from the intended scope of the present invention. The sensors are connected to a high-speed data acquisition means, which records the sensor-generated signals and transmits the data to the programmable control means. Any suitable programmable control means may be used including, without limitation, a laptop computer, a mainframe computer or any other similar microprocessor based device (i.e. central processing unit (CPU)). The high-speed data acquisition means is capable of recording multiple data input. The information obtained by the sensors is used by the programmable control means to controls operational parameters of the power source, the thermo-chemical treatment system and the multifunctional heating/cooling system in order to obtain desired service characteristics of an engineering material.

As mentioned previously, the programmable control means may be a laptop computer or some other form of CPU that is located adjacent the IESV apparatus. Still further, it should be noted that the software of the programmable control means is capable of performing, through a Local Area Network or an Internet connection, the programming, monitoring and controlling of the operating parameters of the electromagnetic treatment procedure. Accordingly, the CPU may be either on-site or off-site. The software controls the operating conditions of the controlled current/voltage source during the electromagnetic treatment process. The software also controls the variable heating and cooling operation parameters of the MEC and the variable operating parameters of the thermo-chemical treatment system. The software also controls, in real-time, the collection, analysis and storage the sensor signals received by the high-speed data acquisition means.

It should be noted that sensors also acquire information about the thermal signature of the treated work piece. The analysis of this sensed data is performed using the Advanced Thermal Analysis methodology, which allows for optimization of the work piece characteristics and process parameters as well as dynamic process control.

In the preferred embodiment of the invention, the heating/cooling means can be applied to the work piece and the MEC coil. According to the preferred embodiment, the programmable control means is capable of delivering a cooling medium from the heating/cooling source to both the internal and external surfaces of the work piece. The programmable control means is also capable of heating the work piece or isothermal holding the work piece during the electromagnetic treatment process.

In a further embodiment of the invention, the apparatus includes a thermo-chemical treatment system, which uses additives such as neutral and reactive gases, solids and powders to improve the metallurgical structure and service characteristics of the work piece.

Figure 1:
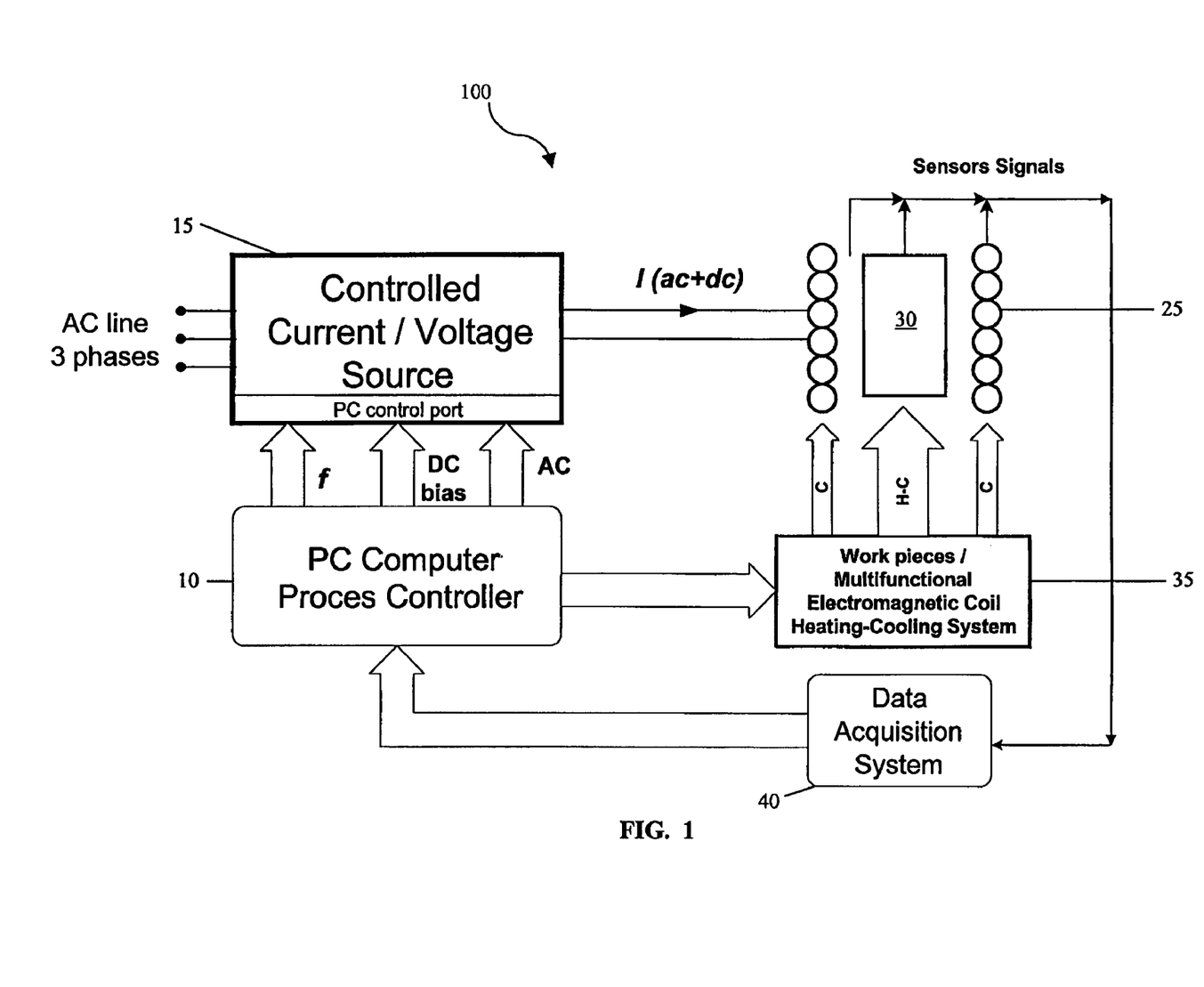
FIG. 1 is a block diagram view of the preferred embodiment of the present invention.
Figure 2:
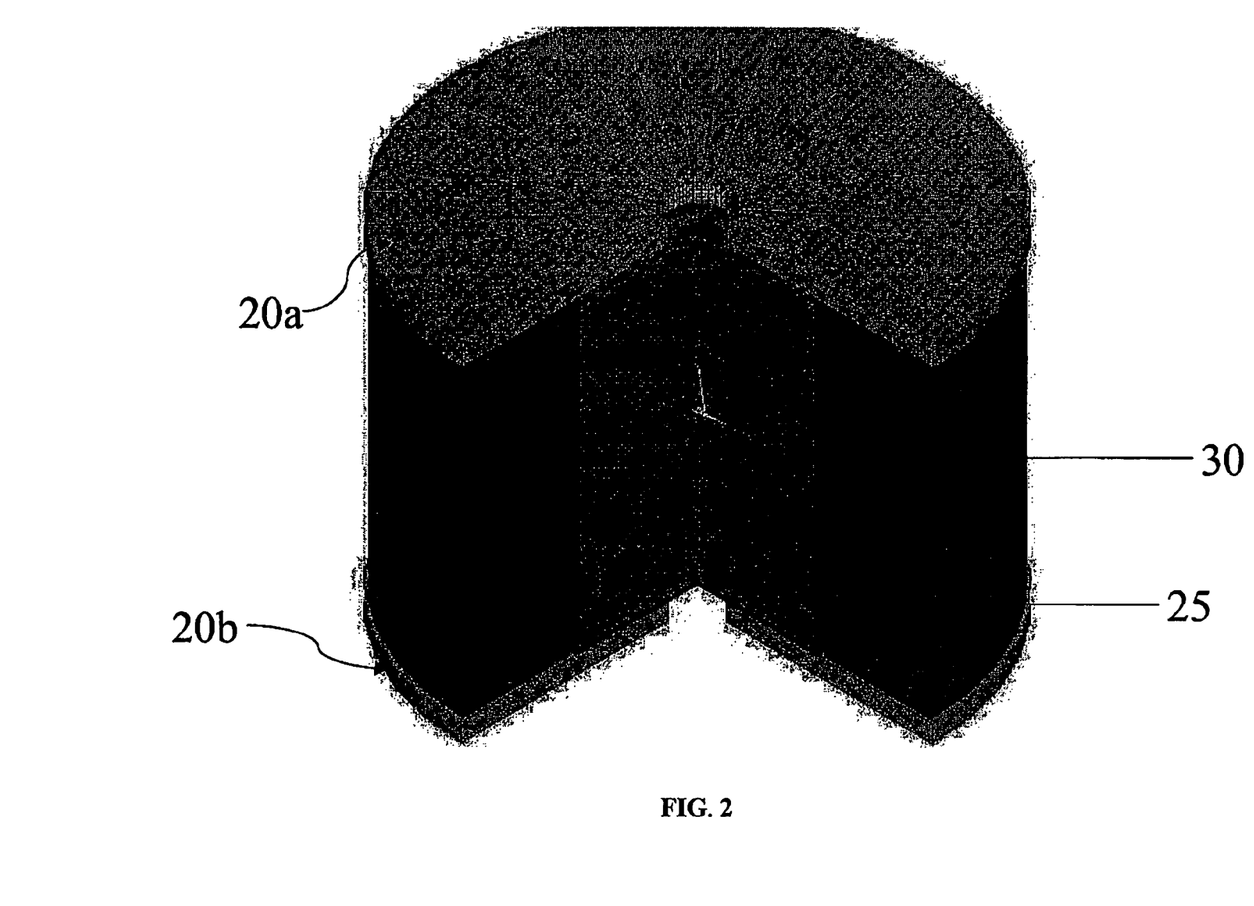
FIG. 2 illustrates a 3-D model of an embodiment of the MEC of the present invention.

With reference to FIG. 1, there is illustrated a block diagram of the preferred embodiment of the present invention. Further, FIG. 2 shows a 3-D view of the electromagnetic coil of the invention. It should be readily understood that while a specific implementation and related configuration are shown, variations may occur in such configuration without straying from the intended scope of the present invention.

With further reference to FIG. 1, there is shown an IESV apparatus 100 including a programmable control means 10 connected to a power supply 15, termed a controlled current/voltage source. The power supply 15 is coupled to an electromagnetic coil (25 in FIG. 2). Enclosed within the electromagnetic cores (20a and 20b in FIG. 2) is a multifunctional electromagnetic coil 25, which surrounds a holder (not shown for clarity of illustration) for a work piece 30. A heating/cooling system 35 is coupled to both the multifunctional electromagnetic coil 25 and the holder 30. Sensors (not shown) are positioned in, on or around the work piece 30 to acquire data. The sensors are coupled to a data acquisition means 40, which in turn is coupled to the programmable control means 10.

The programmable control means 10 controls the ESV apparatus, stores data and analyzes the data acquired by the data acquisition means 40 during the electromagnetic treatment process. The operating parameters of the electromagnetic treatment process are either entered by an operator or copied from a storage memory. The operating parameters may also be adjusted during the electromagnetic treatment process based on the data acquired by the sensors. This allows for precise control of the electromagnetic treatment process and results in the work piece having a more refined metallurgical structure and service characteristics.

According to the present invention, in operation, a superimposed harmonic AC+DC current is generated by the Controlled Current/Voltage Source 15 and transmitted to the Multifunctional Electromagnetic Coil (MEC) 25. The harmonic AC current component generates a multi-harmonic variable magnetic field B(t). As a consequence, eddy currents of density j and frequency $fn$ are generated inside the work piece. The stationary magnetic field B is created by the DC current component. The combined interaction of the eddy currents and electromagnetic fields (stationary and variable) generates the following vibration and stirring forces inside the work piece:

a. The interaction of the stationary magnetic field B and eddy currents having density j produce a vibrating force (j×B) with a frequency $f$. The vibration force is perpendicular to the symmetry axis of the Multifunctional Excitation Coil(s)/work piece(s).
 b. The interaction of the multi-harmonic variable magnetic field B(t) and eddy currents of density j generate the product of electromagnetic forces j×B(t), which consists of the time-independent stirring component and the harmonic component with frequency $2fn$.

The Controlled Current/Voltage Source 15 provides an innovative supply power to the invention. The Controlled Current/Voltage Source 15 is connected to the Multifunctional Electromagnetic Coil(s) and serves as a means for:

a. Generating an Alternating Current (AC) component having harmonic shapes (i.e. sinusoidal, rectangular, triangular, etc. with controlled characteristics.

b. Imposing a Direct Current (DC) with a constant bias on the AC Current.

c. Varying the frequency $f$ of the AC current component.

It should be understood to one having ordinary skill in the art that computer software may be provided to control the operating parameters of the Controlled Current/Voltage Source 15 and allows for a desired setup of the AC and DC operating parameters including their flexible programming for operating the apparatus of the invention.

Vibration forces generate electromagnetic pressure waves within the volume of the work piece. These pressure waves subject the liquid/semi-liquid material to forces of compression and tension in two successive halves of a cycle. As a result of the pressure oscillation in the liquid material, cavities will form and pre-existing gas bubbles will then grow by absorbing dissolved gases and/or material vapour from the surrounding melt under the repetitive compression and expansion. Once the bubbles disappear, extremely powerful shock waves will occur. The aforementioned process is known as the Cavitation Phenomenon, which aids in structure refinement of the liquid/semi-solid work piece.

Figure 3A:
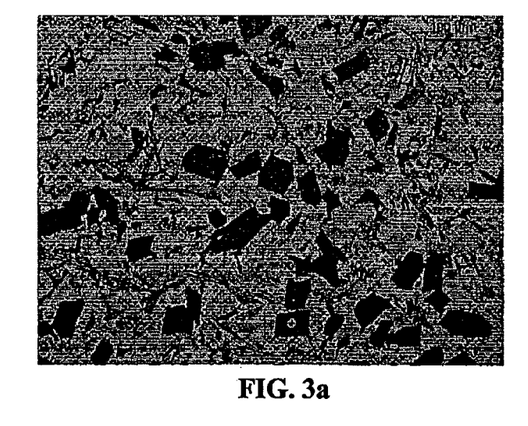
FIGS. 3a and 3b are LOM micrograph views of a hyper-eutectic Al—Si alloy casting before and after treatment by the apparatus of the present invention.
Figure 3B:
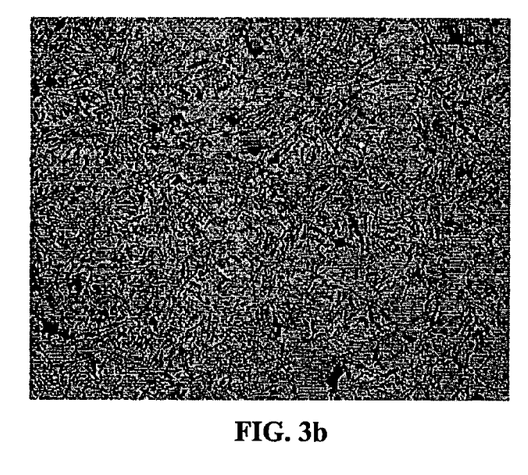

With regards to FIGS. 3a, 3b, two light optical microscope (LOM) micrographs for an example of structural refinement according to the present invention of a hypereutectic Al—Si alloy casting are shown. Electromagnetic treatment according to the present invention was performed above the liquidus temperature prior to the casting operation, rendering a significant improvement in the metallurgical characteristics.

In FIG. 3a, the hypereutectic Al—Si alloy casting has been solidified at a cooling rate of 0.1 C/s without any treatment and FIG. 3b the hypereutectic Al—Si alloy casting has being solidified at a cooling rate of 0.1 C/s and has been subjected to treatment by the IESV apparatus above liquidus temperature. It is apparent from FIGS. 3a and 3b that significant improvements in the metallurgical characteristics including a reduction in secondary dendrite arm spacing and grain size, an amelioration of the casting homogeneity, and constituent size refinement are achieved when the Al—Si alloy is subject to treatment by the apparatus of the present invention. In addition to achieving these desired results, the treated melt's flowability and feedability were also notably improved in comparison to untreated and/or chemically treated melts. Melts subjected to electromagnetic treatment produce very well refined metallurgical structures even in slowly solidified castings.

Figure 4A:
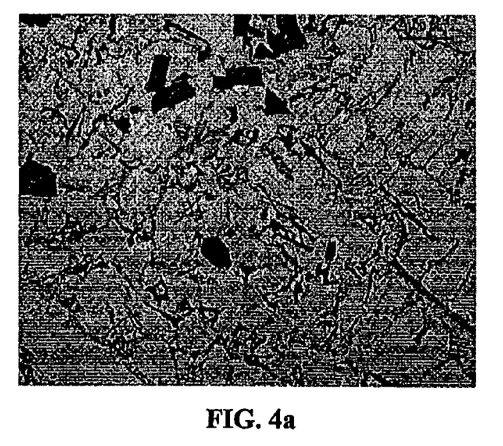
FIGS. 4a and 4b are LOM micrograph views a commercial piston made from a 390 alloy before and after treatment by the apparatus of the present invention.
Figure 4B:
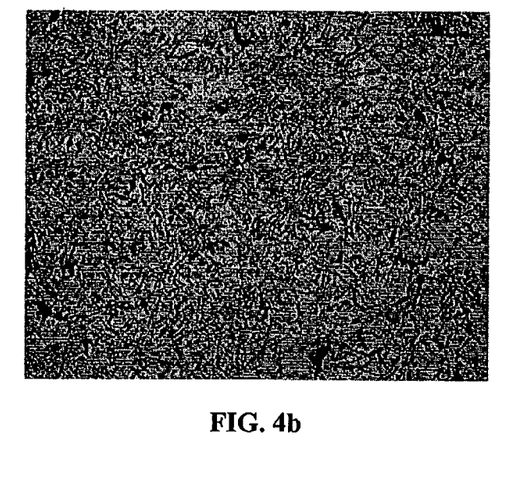
Figure 5A:
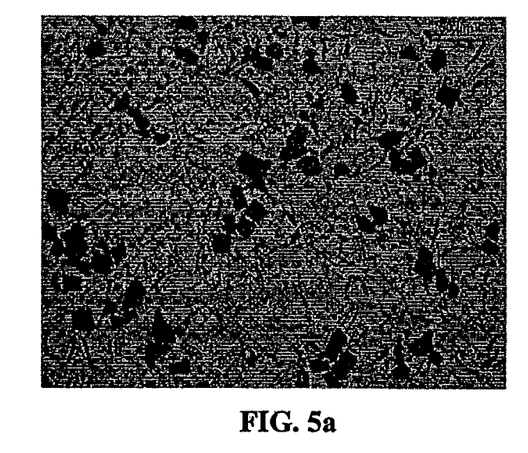
FIGS. 5a and 5b are higher resolution LOM micrograph views shown in FIGS. 4a and 4b.
Figure 5B:
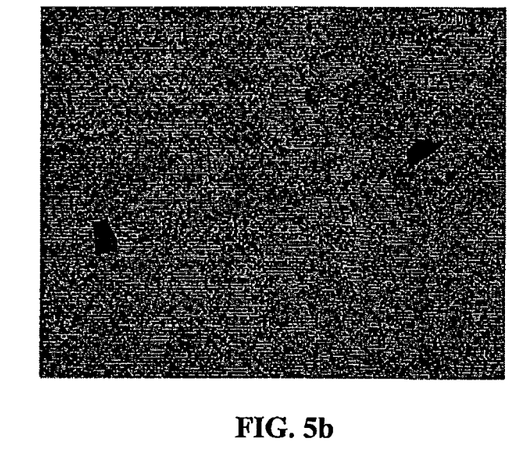
Figure 6A:
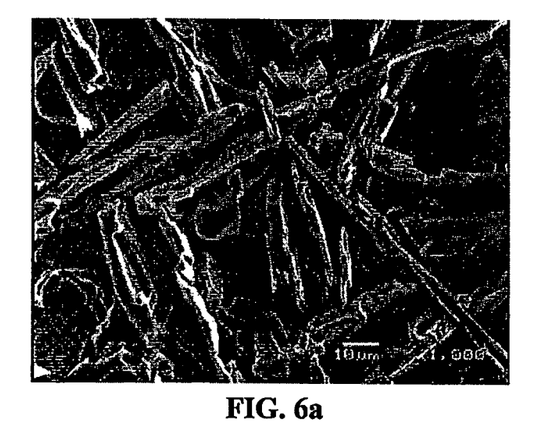
FIGS. 6a and 6b are still higher resolution LOM micrograph views shown in FIGS. 4a and 4b.
Figure 6B:
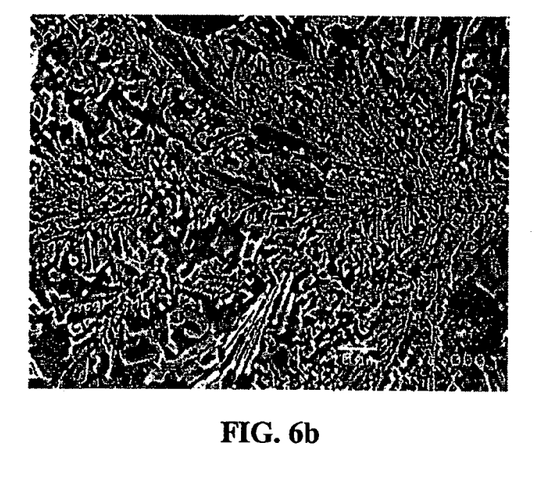

With regards to FIGS. 4a, and 4b, two LOM micrographs of a 390 alloy casting are shown. It should be noted that the LOM micrographs were take with 100× magnification. In both FIGS. 4a and 4b, the 390 alloy casting has been solidified at a slow cooling rate of 0.2 C/s, however the 390 alloy casting of FIG. 4b has been subjected to treatment by the IESV apparatus above liquidus temperature. Again, it is apparent from FIGS. 4a and 4b that significant improvements in the metallurgical characteristics of the 390 alloy are achieved when it is subjected to treatment by the apparatus of the present invention, including a reduction in secondary dendrite arm spacing and grain size, an amelioration of the casting homogeneity and constituent size refinement.

FIGS. 5a, 5b, 6a, and 6b illustrate the same results as in FIGS. 4 and 4b, however the Scanning Electron Microscope (SEM) and LOM micrographs have been taken with a 200× and 1000× magnification.

Figure 7A:
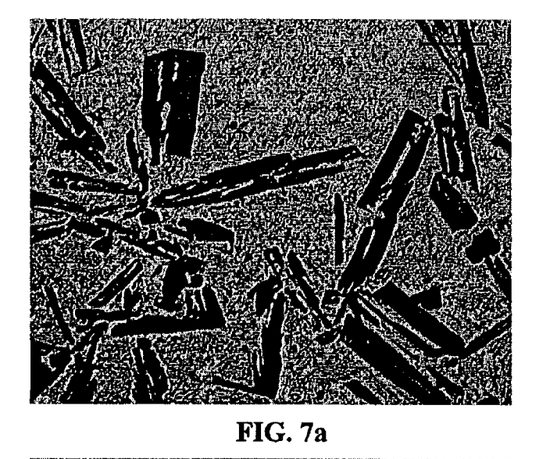
FIGS. 7a and 7b are LOM micrograph views of 25% Si aluminum before and after treatment by the apparatus of the present invention.
Figure 7B:
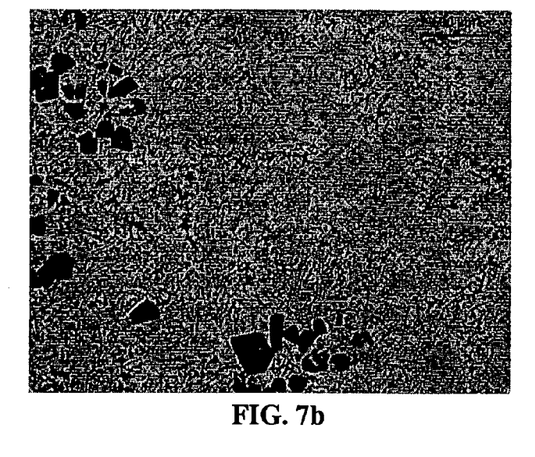

With regards to FIGS. 7a, and 7b, two LOM micrographs of a 25% Si aluminum alloy structure are shown It should be noted that the LOM micrographs were take with 25× magnification. In both FIGS. 7a and 7b, the 25% Si aluminum alloy structure has been solidified at a slow cooling rate of 0.2 C/s, however the 25% Si aluminum alloy structure of FIG. 7b has been subjected to treatment by the IESV apparatus a few degrees below liquidus temperature. Again, it is apparent from FIGS. 7a and 7b that significant improvements in the metallurgical characteristics of the 390 alloy are achieved when it is subjected to treatment by the apparatus of the present invention, including a reduction in secondary dendrite arm spacing and grain size, an amelioration of the casting homogeneity and constituent size refinement.

Figure 8A:
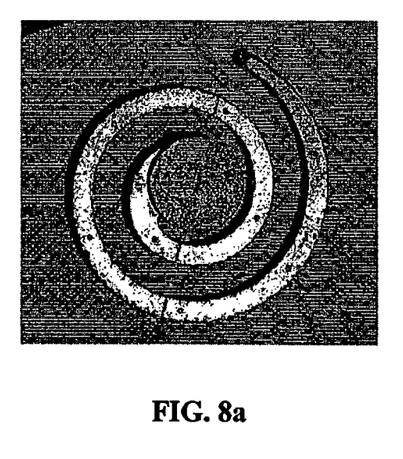
FIG. 8 shows the results of the fluidity spiral tests of the material before and after treatment by the apparatus of the present invention.
Figure 8B:
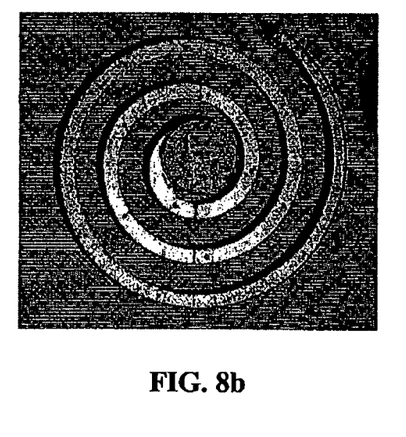

With regards to FIGS. 8a and 8b, the effect of the IESV treatment on the melt flowability a metal is shown. The fluidity spiral test results indicate increased flowability and feedability.

In operation, the IESV inventions structurally refines engineering metallic materials and products for improvement of their processing technologies and service characteristics. The present invention renders significantly better results in comparison to existing technologies. The IESV system can be utilized independently or together with the Universal Metallurgical Simulator and Analyzer (UMSA), as disclosed in U.S. patent application Ser. No. 60/339,358 filed on Dec. 13, 2001 and also filed as PCT Application No. PCT/CA02/01903 filed on Dec. 12, 2002 the contents of both herein incorporated by reference, for given applications as well as rapid melting, heat treatment and quenching operations.

The electromagnetic treatment is performed under customized closed-loop controlled conditions using a wide range of operating parameters in order to achieve optimum results. Metallic materials like pure metals, metal matrix composites and alloys as well as other products, can be treated in liquid, semi-solid and solid states. Processing can be performed under batch and continuous conditions with an unprecedented level of control including the treatment above or below the dendrite coherency temperature. For some applications, maximization of the electromagnetic treatment can be achieved by simultaneous thermo-chemical treatment The IESV system can be utilized for both low and mass volume production and for the development of new engineering materials, processes and products, having simple and/or complex geometries including ingots, shape and continuous castings, and on-demand semi-solid billets used for further processing.

It should be understood that the preferred embodiments mentioned here are merely illustrative of the present invention. Numerous variations in design and use of the present invention may be contemplated in view of the following claims without straying from the intended scope and field of the invention herein disclosed.

Having thus described the invention, what is claimed as new and secured by Letters Patent is:

1. An apparatus for performing electromagnetic treatment on processed metallurgical materials and products, said apparatus comprising:

a holder for a work piece;

a power supply for providing voltage and current to a single electromagnetic coil, said power supply including a means for generating an alternating current component having harmonic shapes with controlled characteristics, a means for imposing a direct current component with a constant bias on said alternating current component, and a means for varying frequency of said alternating current component;

a thermal source for varying temperature of said work piece and said single electromagnetic coil;

at least one sensor;

a data acquisition means for recording data measured by at least one sensor; and a processor for controlling, monitoring, and analyzing at least one operating parameter of said electromagnetic treatment;

wherein said power supply is coupled to said single electromagnetic coil such that said alternating current component and said direct current component are carried over said single electromagnetic coil, said holder is located proximate to said single electromagnetic coil, said thermal source is coupled to said holder and said single electromagnetic coil, and said processor is coupled to said power supply, said data acquisition means, and said thermal source.

2. An apparatus for performing electromagnetic treatment and thermal-chemical treatments simultaneously on processed engineering materials and products, said apparatus comprising:

a holder for a work piece;

a power supply for providing voltage and current to a single electromagnetic coil, said power supoly including a means for generating an alternating current component having harmonic shapes with controlled characteristics, a means for imposing a direct current component with a constant bias on said alternating current component, and a means for varying frequency of said alternating current component;

a heating/cooling source for varying the temperature of said work piece and said single electromagnetic coil;

a thermo-chemical treatment system;

at least one sensor;

a data acquisition means for recording data measured by at least one sensor; and a processor for controlling, monitoring, and analyzing at least one operating parameter of said electromagnetic treatment;

wherein said power supply is coupled to said single electromagnetic coil such that said alternating current component and said direct current component are carried over said single electromagnetic coil, said holder is located proximate to said single electromagnetic coil, said heating/cooling source is coupled to said holder and said single electromagnetic coil, said thermo-chemical treatment system is connected to said work piece, and said processor is coupled to said power supply, said data acquisition means, and said thermal source.

3. An apparatus for optimizing electromagnetic treatment processes for processed engineering materials and products, said apparatus comprising:

a holder for a work piece;

a power supply for providing voltage and current to a single electromagnetic coil, said power supply including a means for generating an alternating current component having harmonic shapes with controlled characteristics, a means for imposing a direct current component with a constant bias on said alternating current component, and a means for varying frequency of said alternating current component;

a thermal source for varying the temperature of said work piece and said single electromagnetic coil;

at least one sensor, a data acquisition means for recording data measured by at least one sensor;

and a computer for controlling, monitoring, and analyzing at least one operating parameter of said electromagnetic treatment and for adjusting at least one operating parameter based on said data acquired by said data acquisition means;

wherein said power supply is coupled to said single electromagnetic coil such that said alternating current component and said direct current component are carried over said single electromagnetic coil, said holder is located proximate to said single electromagnetic coil, said thermal source is coupled to said holder and said single electromagnetic coil, said computer is coupled to said power supply, said data acquisition means, and said thermal source, said computer uses an Advanced Thermal Analysis (ATA) technique to analyze the thermal signature of said work piece during said electromagnetic treatment.

* * * * *